United States Patent [19]

Scharwaechter et al.

[11] 4,189,581
[45] Feb. 19, 1980

[54] 2-ACYLAMINO-4-AMINO-5-(3,4,5-TRIME-THOXYBENZYL)-PYRIMIDINES

[75] Inventors: Peter Scharwaechter, Moorrege; Klaus Gutsche, Rellingen; Friedrich-Wilhelm Kohlmann, Moorrege, all of Fed. Rep. of Germany

[73] Assignee: BASF Aktiengesellschaft, Fed. Rep. of Germany

[21] Appl. No.: 880,884

[22] Filed: Feb. 24, 1978

[30] Foreign Application Priority Data

Mar. 4, 1977 [DE] Fed. Rep. of Germany ....... 2709634

[51] Int. Cl.$^2$ .......................................... C07D 239/48
[52] U.S. Cl. .................................... 544/324; 544/325; 424/229
[58] Field of Search ................................ 544/325, 324

[56] References Cited

U.S. PATENT DOCUMENTS 3,919,229   11/1975   Carraz et al. .................. 544/325

FOREIGN PATENT DOCUMENTS 507243   6/1971   Switzerland ..................... 544/325

Primary Examiner—Paul M. Coughlan, Jr.
Attorney, Agent, or Firm—Keil & Witherspoon

[57] ABSTRACT

2-Acylamino-4-amino-5-benzylpyrimidines substituted in the phenyl ring of the benzyl radical, their production and their use as sulfonamide potentiators, as well as agents containing the same, are disclosed. The compounds 4-amino-2-formamido-5-(3,4,5-trimethoxybenzyl)-pyrimidine and 4-amino-2-acetamido-5-(3,4,5-trimethoxybenzyl)-pyrimidine are examples of the subject pyrimidines.

1 Claim, No Drawings

2-ACYLAMINO-4-AMINO-5-(3,4,5-TRIMETHOXYBENZYL)-PYRIMIDINES

The present invention relates to new benzylpyrimidines of the formula

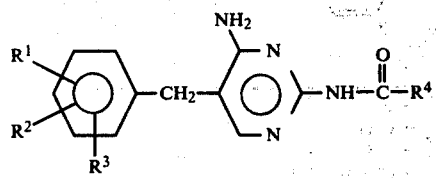

where $R^1$, $R^2$ and $R^3$ are identical or different and each denotes hydrogen, methyl, methoxy or chlorine and $R^4$ denotes hydrogen, carbalkoxy of 1 to b 4 carbon atoms in the alkyl radical, alkyl or alkenyl of 1 to 11 carbon atoms, which may be substituted by carboxy, carbalkoxy of 1 to 4 carbon atoms in the alkyl radical, alkoxy of 1 to 4 carbon atoms in the alkyl radical, nitrile, amino, chlorine, phenoxy—which may be substituted in the phenyl radical by one or more halogen atoms, methyl groups or methoxy groups—or by a cycloaliphatic radical of 5 or 6 carbon atoms in the ring and may be interrupted by one or more oxygen atoms, or an aromatic or araliphatic radical of 6 to 10 carbon atoms which may be mono- to trisubstituted in the aromatic ring by halogen atoms, methyl groups or methoxy groups or substituted by a carboxy group or carbalkoxy group of 1 to 4 carbon atoms in the alkyl, or a 5- or 6-membered heterocyclic aromatic ring which contains one or more nitrogen, oxygen and/or sulfur atoms and may be substituted by methyl, or a mono- or polycyclic cycloaliphatic ring of 3 to 10 carbon atoms which may be substituted by carboxy and may contain a double bond.

Substituents $R^1$, $R^2$ and $R^3$ are preferably at positions 3, 4 and 5 of the benzyl ring. If $R^4$ is alkyl or alkylene of 1 to 11 carbon atoms which are interrupted by several oxygen atoms, the oxygen atoms are separated from each other by at least 2 carbon atoms, as is the case for example when $R^4$ is methoxyethoxymethyl.

Among the carbalkoxy radicals which $R^4$ may renote, carbethoxy is particularly suitable. Especially suitable alkyl radicals for $R^4$ are linear or branched radicals of 1 to 9 carbon atoms which may be substituted particularly by a carboxy group, a carbalkoxy group of 1 to 4 carbon atoms in the alkyl, an alkoxy group of 1 to 4 carbon atoms in the alkyl, a phenoxy group whose phenyl ring may be additionally substituted by 1 or 2 chlorine atoms, or a 5- or 6-membered cycloaliphatic radical, or may contain a carbonyl group in the aliphatic chain.

Examples of aromatic radicals suitable for $R^4$ are especially phenyl or naphthyl radicals which may be mono- to trisubstituted especially by 1 to 3 methoxy groups, methyl groups and/or chlorine atoms or monosubstituted by carboxy or carbalkoxy of 1 to 4 carbon atoms in the alkyl.

Examples of araliphatic radicals suitable for $R^4$ are especially benzyl and phenylethyl which may be substituted especially by fluorine or chlorine.

Examples of suitable cycloaliphatic radicals are especially mono- and tricyclic rings, such as cyclopropyl, cyclopentyl, cyclohexyl, adamantyl, tetrahydronaphthyl and cyclohexenyl, which may be substituted by a carboxy radical.

Examples of heterocyclic radicals suitable for $R^4$ are especially those having 5 or 6 atoms in the ring and which contain either one hetero atom alone or one nitrogen atom together with another, different hetero atom in the ring, or contain, in addition to nitrogen as hetero atom, two or three identical hetero atoms in the ring. The heterocyclic radicals may be aromatic, unsaturated or saturated. They may contain additional hetero atoms of the kind indicated above outside the ring, e.g. in amino, hydroxy or oxy groups. Preferred heterocycles for $R^4$ are isoxazole, thiophene and pyridine, which may be substituted by methyl.

Among the compounds of formula I those are particularly preferred in which $R^1$, $R^2$ and $R^3$ denote methyl or methoxy, especially those compounds in which substituents $R^1$, $R^2$ and $R^3$ are at positions 3, 4 and 5 of the benzyl radical, above all trimethoxybenzyl.

The compounds of formula I are antibacterial and, in combination with antibacterial sulfonamides, potentiate the latter's antibacterial effect, e.g. in bacterial diseases of the respiratory organs, digestive organs and urethras as well as in otorhinolaryngological infections and general systemic infectious diseases.

Examples of such sulfonamides are sulfadiazine (2-sulfanilamidopyrimidine), sulfamonomethoxine, sulfadimethoxine, sulfamethoxazole, sulfamoxole, 2-sulfa-4,5-dimethyl-isoxazole and 4-sulfanilamido-5,6-dimethoxy-pyrimidine.

The compounds of formula I may be combined with the sulfonamides given as examples in various relative proportions, the ratio of compound of formula I to conventional sulfonamide ranging from 1:10 to 5:1. Preferred relative proportions are 1:1 to 1:5. As a rule, a suitble single dose of an active ingredient of formula I is from 20 to 500 mg.

The compounds of formula I, according to the invention, are prepared by the methods conventionally used for the production of carboxamides, in which a compound of the general formula II

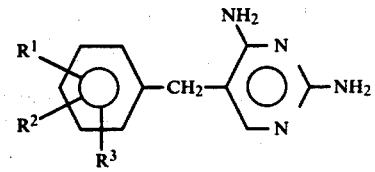

where $R^1$, $R^2$ and $R^3$ have the above meanings, is reacted with a carboxylic acid derivative, conventionally used for the production of acid amides, of the general formula III

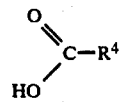

where $R^4$ has the above meaning, advantageously in a solvent and at from 20° to 200° C. and, optionally, in the presence of an acidbinding agent, and, in the event that intermediate products are formed, these intermediates are converted into the desired products of formula I in a further step.

Examples of carboxylic acid derivatives suitable for the preparation of the compounds according to the invention are acid chlorides, acid anhydrides and orthocarboxylic acid esters. This enumeration of suitable carboxylic acid derivatives is not to be interpreted as a restriction with regard to the derivatives usually used for carboxamide syntheses; however, the types of compounds indicated above are preferred in the production of the compounds of the invention. When $R^4$ denotes a hydrogen atom, a mixed acid anhydride, e.g. formic/acetic acid anhydride, is employed; otherwise, symmetrical acid anhydrides are usually used. Preferred ortho esters are triethyl and trimethyl esters.

Depending on the nature of the substituent $R^4$ in the carboxylic acid derivatives used, the acylation of the starting compounds of formula II leads either directly to the compounds according to the invention or to intermediate products acylated at both amino groups attached to the pyrimidine ring, from which intermediate products the acyl radical attached to the amino group located at position 4 is removed again by partial hydrolysis.

Hydrolysis is advantageously carried out at room temperatures in a lower alcohol as solvent and in the presence of one equivalent of alkali.

When ortho esters are used for acylation it may be necessary to convert any imino esters formed as intermediate products into the compounds of the invention by partial hydrolysis, unless they change of their own accord to the compounds of the invention during the processing of the reaction mixtures.

Acylation of the compounds of formula II may be carried out in the presence or absence of a solvent; the solvent may, in the form of a tertiary base, such as pyridine, simultaneously serve as an acid-binding agent. The starting product of formula II may itself serve as the acid-binding agent, as may other tertiary bases, such as triethylamine and trimethylamine.

All conventionally used aprotic solvents are suitable as solvents for the acylation reaction. Preferred solvents are dioxane, chloroform, pyridine and chlorobenzene, since the starting products of formula II dissolve readily in them. The acylation is preferably carried out in a temperature range of from 50° to 150° C.

In order to prove the effectiveness of the substances according to the invention, they were tested on mice, in accordance with the Aronson sepsis model, infection being effected with *Streptococcus Agalaciae*, and compared with the well-known trimethoprim. For this purpose, groups of 30 female mice were inoculated with a lethal dose of streptococcus agalactiae 7941 and treated two hours later with a mixture of 300 mg of 2-sulfanilamido-4,5-dimethyloxazole and 60 mg of one of the substances of the invention. Apart from a non-treated control group, a second group was treated with the reference substance, namely a mixture of 300 mg of 2-sulfanilamido-4,5-dimethyloxazole and 60 mg of trimethoprim. After 44 hours the number of surviving animals was determined. This number was divided by the number of surviving animals in the group treated with the reference substance. The numerical value obtained (trimethoprim factor) is a measure of the effect of the substances of the invention as compared with that of trimethoprim. Thus, F=2 means tht the substance concerned is twice as effective as trimethoprim. As may be seen from the following table, the substances of the invention are up to 3.5 times as effective as trimethoprim.

Table I

General formula:

$$\text{(CH}_3\text{O)}_3\text{-Ar-CH}_2\text{-[pyrimidine with NH}_2\text{ at 4, NH-C(=O)-R}^4\text{ at 2]}$$

| No. | $R^4$ | F |
|---|---|---|
| 1 | —H | 2.0 |
| 2 | —CH$_3$ | 2.0 |
| 3 | —C$_2$H$_5$ | 1.7 |
| 4 | —(CH$_2$)$_4$—CH$_3$ | 1.5 |
| 5 | —(CH$_2$)$_8$—CH=CH$_2$ | 1.4 |
| 6 | —CHCl$_2$ | 2.7 |
| 7 | —C(CH$_3$)$_3$ | 3.5 |
| 8 | —C$_2$H$_4$—COOH | 1.2 |
| 9 | —COOC$_2$H$_5$ | 1.7 |
| 10 | —C$_6$H$_5$ (phenyl) | 1.2 |
| 11 | —C$_6$H$_4$—Cl (4-chlorophenyl) | 1.2 |
| 12 | 5-methyl-isoxazol-3-yl | 1.3 |
| 13 | —C$_6$H$_4$—OCH$_3$ / Cl (methoxy-chlorophenyl) | 2.0 |
| 14 | cyclohexenyl-COONa | 1.3 |
| 15 | —CH$_2$—C$_6$H$_{11}$ (cyclohexylmethyl) | 1.5 |
| 16 | —CH(cyclopropyl) | 1.2 |
| 17 | thienyl (S) | 2.0 |
| 18 | —CH$_2$—C$_6$H$_4$—Cl | 1.7 |
| 19 | —CH$_2$—O—C$_6$H$_4$—Cl | 3.0 |
| 20 | —CH$_2$—O—C$_6$H$_3$Cl$_2$ (2,4-dichlorophenoxymethyl) | 1.5 |

Table I-continued

General formula

CH₃O—, CH₃O—, CH₃O— substituted benzyl-CH₂- attached to pyrimidine ring with NH₂ and two N, with —NH—C(=O)—R⁴

| No. | R⁴ | F |
|---|---|---|
| 21 | —CH₂—C₆H₄—F | 2.25 |
| 22 | cyclohexyl (H) | 1.3 |
| 23 | adamantyl | 1.0 |
| 24 | —CH(C₂H₅)₂ | 1.0 |
| 25 | —C₂H₄—CO₂CH₃ | 1.25 |

Accordingly, the present invention also relates to chemotherapeutic agents that contain a compound of formula I as active ingredient, especially in combination with a sulfonamide, together with conventional excipients and diluents, and to the use of the compounds of formula I as sulfonamide potentiators.

The chemotherapeutic agents or formulations are prepared in the conventional manner using the conventional excipients or diluents and the conventional pharamaceutical auxiliaries, in accordance with the desired route of administration.

The preferred formulations are those suitable for oral administration. Examples of these are tablets, film tablets, dragees, capsules, pills, powders, solutions or suspensions.

The Examples that follow illustrate the invention.

EXAMPLE 1

2.64 g of formic acid/acetic acid anhydride are dripped, while cooling, into a suspension of 2.9 g of 2,4-diamino-5-(3,4,5-trimethoxybenzyl)-pyrimidine (trimethoprim) in 35 ml of pyridine and reacted at 50° to 60° C. for two hours. The reaction mixture is then poured into 400 ml of water and the precipitate is filtered off and recrystallized from a mixture of dimethyl-formamide and water. 2.4 g (75% of theory) of 4-amino-2-formamido-5-(3,4,5-trimethoxybenzyl)-pyrimidine of melting point 240° to 242° C. are obtained.

The following substances are synthesized analogously using the appropriate symmetrical anhydride:

4-amino-2-acetamido-5-(3,4,5-trimethoxybenzyl)-pyrimidine, m.p. 214° C.
4-amino-2-valeramido-5-(3,4,5-trimethoxybenzyl)-pyrimidine, m.p. 150° C.
4-amino-2-isovaleramido-5-(3,4,5-trimethoxybenzyl)-pyrimidine, m.p. 148° C.
4-amino-2-pivaloamido-5-(3,4,5-trimethoxybenzyl)-pyrimidine, m.p. 107° C.
4-amino-2-benzamido-5-(3,4,5-trimethoxybenzyl)-pyrimidine, m.p. 191° C.

EXAMPLE 2

5.8 g of 2,4-diamino-5-(3,4,5-trimethoxybenzyl)-pyrimidine (trimethoprim) are suspended in 58 ml of chlorobenzene. At 125° C., 1.55 g of phenylacetyl chloride are dripped in, and the whole is maintained at this temperature for five hours. The difficultly soluble trimethoprim hydrochloride is filtered off and the filtrate is concentrated in vacuo. Upon recrystallization from ethanol there is obtained 4-amino-2-phenylacetamido-5-(3,4,5-trimethoxybenzyl)-pyrimidine of melting point 181° to 183° C.

The following substances are prepared analogously:

4-amino-2-benzamido-5-(3,4,5-trimethoxybenzyl)-pyrimidine, m.p. 190° C.
4-amino-2-(p-chlorbenzamido)-5-(3,4,5-trimethoxybenzyl)-pyrimidine, m.p. 197° C.
4-amino-2-(3,4,5-trimethoxybenzamido)-5-(3,4,5-trimethoxybenzyl)-pyrimidine, m.p. 222° C.
4-amino-2-(phenoxyacetamido)-5-(3,4,5-trimethoxybenzyl)-pyrimidine, m.p. 170° C.
4-amino-2-(cyclohexylacetamido)-5-(3,4,5-trimethoxybenzyl)-pyrimidine, m.p. 178° C.
4-amino-2-(capronamido)-5-(3,4,5-trimethoxybenzyl)-pyrimidine, m.p. 167° C.
4-amino-2-heptanoylamido-5-(3,4,5-trimethoxybenzyl)-pyrimidine, m.p. 132° C.
4-amino-2-nonanoylamido-5-(3,4,5-trimethoxybenzyl)-pyrimidine, m.p. 137° C.
4-amino-2-caprinamido-5-(3,4,5-trimethoxybenzyl)-pyrimidine, m.p. 116° C.
4-amino-2-(10-undecenoylamido)-5-(3,4,5-trimethoxybenzyl)-pyrimidine, m.p. 129° C.
N-[4-amino-5-(3,4,5-trimethoxybenzyl)-pyrimidin-2-yl]-oxamic acid ethyl ester, m.p. 151° C.
N-[4-amino-5-(3,4,5-trimethoxybenzyl)-pyrimidin-2-yl]-glutaric acid amide methyl ester, m.p. 159° C.
4-amino-2-(4-fluorophenylacetamido)-5-(3,4,5-trimethoxybenzyl)-pyrimidine, m.p. 194° C.
4-amino-2-cyclohexylcarboxamido-5-(3,4,5-trimethoxybenzyl)-pyrimidine, m.p. 162° C.
4-amino-2-adamantylcarboxamido-5-(3,4,5-trimethoxybenzyl)-pyrimidine, m.p. 237° C.
4-amino-2-diethylacetamido-5-(3,4,5-trimethoxybenzyl)-pyrimidine, m.p. 168° C.
4-amino-2-dichloroacetamido-5-(3,4,5-trimethoxybenzyl)-pyrimidine, m.p. 178° C.
4-amino-2-trichloroacetamido-5-(3,4,5-trimethoxybenzyl)-pyrimidine, m.p. 234° C.
4-amino-2-nicotinoylamido-5-(3,4,5-trimethoxybenzyl)-pyrimidine, m.p. 208° C.
4-amino-2-(4-chlorophenylacetamido)-5-(3,4,5-trimethoxybenzyl)-pyrimidine, m.p. 200° C.
4-amino-2-(4-chlorophenoxyacetamido)-5-(3,4,5-trimethoxybenzyl)-pyrimidine, m.p. 190° C.
4-amino-2-(2,4-dichlorophenoxyacetamido)-5-(3,4,5-trimethoxybenzyl)-pyrimidine, m.p. 193° C.

EXAMPLE 3

34.8 g of 2,4-diamino-5-(3,4,5-trimethoxybenzyl)-pyrimidine and 97.2 g of triethyl orthoacetate are suspended in 240 ml of dimethylformamide and 1.2 ml of concentrated hydrochloric acid. The whole is stirred at 80° to 90° C. for 4 hours, treated with activated carbon and subjected to filtration, and the filtrate is concentrated in vacuo. The crude product obtained is dissolved in 250 ml of water and 60 ml of 2 N hydrochloric acid at 60° C. Upon cooling, the hydrochloride of 4-amino-2-acetamido-5-(3,4,5-trimethoxybenzyl)-pyrimidine of melting point 270° C. crystallizes out. After treatment with 10% strength sodium hydroxide solution 27.6 g of 4-amino-2-acetamido-5-(3,4,5-trimethoxybenzyl)-pyrimidine of melting point 214° C. are obtained.

The following substances are prepared analogously:

4-amino-2-formamido-5-(3,4,5-trimethoxybenzyl)-pyrimidine, m.p. 239° C.
4-amino-2-propionamido-5-(3,4,5-trimethoxybenzyl)-pyrimidine, m.p. 175° C.
4-amino-2-propionamido-5-(3,4,5-trimethoxybenzyl)-pyrimidine hydrochloride, m.p. 275° C.
4-amino-2-butyramido-5-(3,4,5-trimethoxybenzyl)-pyrimidine, m.p. 164° C.
4-amino-2-isobutyramido-5-(3,4,5-trimethoxybenzyl)-pyrimidine, m.p. 186° C.

EXAMPLE 4

5.8 g of trimethoprim are suspended in 80 ml of chloroform. After addition of 4 g of triethylamine 2.5 g of ethoxyacetyl chloride are dripped in at room temperature. The mixture is stirred for another hour at 50° C. and then cooled. The triethylammonium chloride is separated by filtration, the filtrate is concentrated and the residue is recrystallized from isopropanol. 4 g of 2-ethoxyacetamido-4-amino-5-(3,4,5-trimethoxybenzyl)-pyrimidine of melting point 175° to 176° C. are obtained.

The following substances are prepared analogously:

2-(methoxyethoxyacetamido)-4-amino-5-(3,4,5-trimethoxybenzyl)-pyrimidine, m.p. 140° C.
2-cyclopropylcarboxamido-4-amino-5-(3,4,5-trimethoxybenzyl)-pyrimidine, m.p. 186° to 187° C.
2-(5-methylisoxazolcarboxylic acid-3-amido)-4-amino-5-(3,4,5-trimethoxybenzyl)-pyrimidine, m.p. 207° to 209° C.
2-(thiophenecarboxylic acid-2-amido)-4-amino-5-(3,4,5-trimethoxybenzyl)-pyrimidine, m.p. 201° to 203° C.
2-(4-carboethoxybenzoylamino)-4-amino-5-(3,4,5-trimethoxybenzyl)-pyrimidine, m.p. 193° C.
2-(2,4,6-trimethylbenzoylamino)-4-amino-5-(3,4,5-trimethoxybenzyl)-pyrimidine, m.p. 280° to 282° C.
2-(2-methoxy-5-chlorobenzoylamino)-4-amino-5-(3,4,5-trimethoxybenzyl)-pyrimidine, m.p. 138° C.
2-carbomethoxyacetylamino-4-amino-5-(3,4,5-trimethoxybenzyl)-pyrimidine, m.p. 155° C.
2-(β-carbomethoxypropionamido)-4-amino-5-(3,4,5-trimethoxybenzyl)-pyrimidine, m.p. 152° C.

EXAMPLE 5

(a) 8.7 g of trimethoprim are dissolved in 50 ml of pyridine at about 50° C., and then 4.5 g of phthalic anhydride are added. The mixture is stirred for another two hours at from 80° to 90° C.; after cooling, 100 ml of water are added. The precipitate is washed with water and recrystallized from ethanol. 7 g of 2-phthalimido-4-amino-5-(3,4,5-trimethoxybenzyl)-pyrimidine of melting point 221° C. are obtained as intermediate product.

(b) 2.1 g of this product are dissolved in 50 ml of ethanol and refluxed with 5 ml of 1 N sodium hydroxide solution for 2 hours. The precipitate is separated by filtration and washed with ethanol. There are obtained 2 g of the sodium salt of 2-(2-carboxybenzoylamino)-4-amino-5-(3,4,5-trimethoxybenzyl)-pyrimidine, which does not melt at temperatures up to 320° C.

There are obtained in an analogous manner:
from trimethoprim and hexahydrophthalic anhydride via the sodium salt of 2-hexahydrophthalimido-4-amino-5-(3,4,5-trimethoxybenzyl)-pyrimidine of melting point 178° C. the sodium salt of 2-(2-carboxycyclohexanecarboxamido)-4-amino-5-(3,4,5-trimethoxybenzyl)-pyrimidine of melting point 185° C., from trimethoprim and tetrahydrophthalic anhydride via 2-tetrahydrophthalimido-4-amino-5-(3,4,5-trimethoxybenzyl)-pyrimidine of melting point 192° C. the sodium salt of 2-(2-carboxy-1,2,5,6-tetrahydrobenzoylamino)-5-(3,4,5-trimethoxybenzyl)-pyrimidine of melting point 180° C., from trimethoprim and succinic anhydride the 2-succinoylamino-4-amino-5-(3,4,5-trimethoxybenzyl)-pyrimidine of melting point 223° C.

EXAMPLE 6

4.6 g of 2,4-diamino-5-(4-chlorobenzyl)-pyrimidine and 40 ml of acetic anhydride are refluxed for 2.5 hours. The acetic anhydride is then distilled off in vacuo. The residue is stirred into 100 ml of water and adjusted to pH 7 to 8 with ammonia.

A precipitate of 5.6 g of 2,4-diacetylamino-5-(4-chlorobenzyl)-pyrimidine of melting point 147° C. is obtained as intermediate product.

3.2 g of this product are stirred with 10 ml of 1 N sodium hydroxide solution in 50 ml of ethanol for 2 hours at room temperature. The precipitate is separated by filtration and recrystallized from ethanol. Approximately 2 g of 2-acetamido-4-amino-5-(4-chlorobenzyl)-pyrimidine of melting point 219° to 221° C. are obtained.

There are obtained in an analogous manner:
from 2.4-diamino-5-(4-methoxybenzyl)-pyrimidine: 2,4-diacetamido-5-(4-methoxybenzyl)-pyrimidine of melting point 215° C. and 2-acetamido-4-amino-5-(4-methoxybenzyl)-pyrimidine of melting point 203° C., from 2.4-diamino-5-(4-methylbenzyl)-pyrimidine: 2,4-diacetamido-5-(4-methylbenzyl)-pyrimidine of melting point 195° C. as intermediate product and 2-acetamido-4-amino-5-(4-methylbenzyl)-pyrimidine of melting point 213° to 215° C., from 2.4-diamino-5-(2,4-dimethoxybenzyl)-pyrimidine: 2,4-diacetamido-5-(2,4-dimethoxybenzyl)-pyrimidine of melting point 215° C. as intermediate product and 2-acetamido-4-amino-5-(2,4-dimethoxybenzyl)-pyrimidine of melting point 200° C., from 2.4-diamino-5-(3,4-dimethoxybenzyl)-pyrimidine: 2,4-diacetamido-5-(3,4-dimethoxybenzyl)-pyrimidine of melting point 184° C. as intermediate product and 2-acetamido-4-amino-5-(3,4-dimethoxybenzyl)-pyrimidine of melting point 211° C., from 2.4-diamino-5-(2-chlorobenzyl)-pyrimidine: 2,4-diacetamido-5-(2-chlorobenzyl)-pyrimidine of melting point 182° C. as intermediate product and 2-acetamido-4-amino-5-(2-chlorobenzyl)-pyrimidine of melting point 195° C.

EXAMPLES OF FORMULATIONS 400 mg of 2-sulfanilamido-4,5-dimethyloxazole
80 mg of 2-acetylamino-4-amino-5-(3,4,5-trimethoxybenzyl)-pyrimidine
20 mg of corn starch

|   |   |
|---|---|
| 10 mg of | gelatin |
| 8 mg of | talc |
| 2 mg of | magnesium stearate |
| 20 mg of | primojel |

The active ingredients are mixed with corn starch and granulated with aqueous gelatin solution. The dry granules are passed through a sieve and mixed with the additives. The resulting mixture is molded into tablets in conventional manner.

|   |   |
|---|---|
| 160 mg of | 2-sulfanilamido-4,5-dimethyloxazole |
| 80 mg of | 2-acetylamino-4-amino-5-(3,4,5-trimethoxybenzyl)-pyrimidine |
| 5 mg of | gelatin |
| 30 mg of | corn starch |
| 4 mg of | talc |
| 1 mg of | magnesium stearate. |

The active ingredients are granulated with aqueous gelatin solution, and the granules are dried and mixed with corn starch, talc and magnesium stearate. The resulting mixture is molded into tablets in conventional manner.

|   |   |
|---|---|
| 0.200 g of | 2-sulfanilamido-4,5-dimethyloxazole |
| 0.100 g of | acetylamino-4-amino-5-(3,4,5-trimethoxybenzyl)-pyrimidine |
| 1.9 g of | Tylose C 30 |
| 30.0 g of | sugar |
| 10.0 g of | glycerol |
| 2.5 g of | bentonite |
| 0.06 g of | flavoring |
| 0.04 g of | Nipagin M |
| 0.06 g of | Nipasol-sodium |
| | demineralized water to make up to 100.00 g. |

The extremely finely ground active ingredients are suspended in the aqueous Tylose. Then all other ingredients are successively stirred in. Finally water is added to make up to 100.0 g.

We claim:

1. Benzylpyrimidines of the formula I

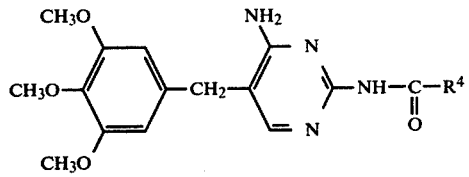

wherein $R^4$ denotes hydrogen; carbalkoxy of 1 to 4 carbon atoms in the alkyl radical; alkyl of 1 to 11 carbon atoms; alkyl of 1 to 11 carbon atoms which is substituted by carboxy, carbalkoxy of 1 to 4 carbon atoms in the alkyl radical, alkoxy of 1 to 4 carbon atoms in the alkyl radical, nitrile, amino, chlorine, phenoxy, phenoxy which is mono- or disubstituted in the phenyl radical by halogen, methyl or methoxy, or by cycloalkyl of 5 to 6 ring carbon atoms; alkenyl of 2 to 11 carbon atoms; methoxyethoxymethyl; phenyl; benzyl; phenylethyl; phenyl, benzyl or phenylethyl which is mono- to trisubstituted in the phenyl radical by halogen, methyl or methoxy; phenyl, benzyl or phenylethyl which is substituted in the phenyl radical by carboxy or carbalkoxy of 1 to 4 carbon atoms in the alkyl; cyclopropyl; cyclopentyl; cyclohexyl; tetrahydronaphthyl; cyclohexenyl; cyclopropyl, cyclopentyl, cyclohexyl, tetrahydronaphthyl or cyclohexenyl which is substituted by carboxy; adamantyl; isoxazolyl; thienyl; pyridinyl; or adamantyl, isoxazoyl, thienyl or pyridinyl which is substituted by methyl.

* * * * *